(12) United States Patent
Fleischner

(10) Patent No.: US 6,420,350 B1
(45) Date of Patent: Jul. 16, 2002

(54) WEIGHT LOSS PRODUCT

(75) Inventor: Albert M Fleischner, Westwood, NJ (US)

(73) Assignee: Goen Group, Inc., Cedar Knolls, NJ (US)

( * ) Notice: Subject to any disclaimer, the term of this patent is extended or adjusted under 35 U.S.C. 154(b) by 0 days.

(21) Appl. No.: 09/928,715

(22) Filed: Aug. 13, 2001

Related U.S. Application Data

(63) Continuation-in-part of application No. 09/761,622, filed on Jan. 18, 2001.

(51) Int. Cl.[7] .......................... A01N 43/04; A61K 31/70
(52) U.S. Cl. .......................... 514/62; 514/909; 424/725; 424/729
(58) Field of Search ................................ 424/725, 729; 514/62, 909

(56) References Cited

U.S. PATENT DOCUMENTS 5,730,988 A * 3/1998 Womack .................. 424/195.1
5,795,576 A * 8/1998 Diaz et al. ............... 424/195.1
5,888,514 A * 3/1999 Weisman ................. 424/195.1

OTHER PUBLICATIONS http://www.nutrasentials.com/TrimSpaOriginal.html—(2000).*
"Green tea and thermogenesis: interactions between catechin–polyphenols, caffeine and sympathetic activity" Dulloo et al. Int. J. of Obesity vol. 24. pp 252–258 (2000).*

* cited by examiner

Primary Examiner—Paul J. Killos
Assistant Examiner—Zachary Tucker
(74) Attorney, Agent, or Firm—Pharmaceutical Patent Attys, LLC; Mark Pohl, Esq.

(57) ABSTRACT

Supplement compositions designed to support weight loss and increase energy.

7 Claims, No Drawings

WEIGHT LOSS PRODUCT

This application is a continuation-in-part of Ser. No. 09/761,622, filed Jan. 18, 2001.

BACKGROUND

The prior art regarding this invention arises from distinct areas not heretofore combined to create new and useful formula sets or new and useful improvements thereof regarding a Solid-dosage Form of a Weight Loss Product.

This invention relates to the evolving science that a new and unique combination of ma huang extract (ephedrine alkaloids), caffeine and glucosamine sulfate results in increased weight loss and energy.

Ma huang is a central nervous system stimulant that has the ability to open up the adrenergic receptor sites found primarily in the heart and lungs, thereby increasing the metabolic rate and calorie expenditure. The net result is the release of fatty acids from stored fat cells and a quicker conversion of the fat into energy. When combined with a modest amount of caffeine the thermogenic effects can be improved as much as 20%[1]. Ma huang also acts as an appetite suppressant.[2]

A double-blind, placebo-controlled study published in Metabolism finds a thermogenic synergism between ephedrine and caffeine.[3] A second study published in the International Journal of Obesity Related Metabolic Disorders concludes that the ephedrine/caffeine combination is safe and effective in long-term treatment in improving and maintaining weight loss.[4] A third study, published in the American Journal of Clinical Nutrition, concludes that results show that ephedrine and caffeine can promote weight loss through an increase in energy expenditure or, in some individuals, a combination of an increase in energy expenditure and a decrease in food intake.[5]

In addition, the ephedrine/caffeine combination has lean body mass saving properties[6,7] and abolishes the decline in HDL-cholesterol during active weight loss due to the beta-agonistic properties of ephedrine.[8] Due to increased central nervous system stimulation, the combination significantly prolongs exercise time to exhaustion and improves performance in runners.[9, 10]

Green tea leaf (camellia sinensis) extract stimulates brown adipose tissue thermogenesis to an extent that is much greater than can be attributed to its caffeine content per se; its thermogenic properties reside primarily in an interaction between its high content in catechin-polyphenols and caffeine with sympathetically released noradrenaline (NA). Green tea extract is effective in stimulating thermogenesis by relieving inhibition at different control points along the NA-cAMP axis. Such synergistic interaction between catechin-polyphenols and caffeine to augment and prolong sympathetic stimulation of thermogenesis has value in assisting the management of obesity.[11]

Epigallocatechin gallate from green tea polyphenols significantly reduced food intake, body weight, blood cholesterol and triglyceride, as well as growth of the prostate, uterus, and ovary; it may interact specifically with a component of a leptin-independent appetite control pathway. [12] Green tea clearly has thermogenic properties, promotes fat oxidation[13] and plays a role in the control of body composition via sympathetic activation of thermogenesis, fat oxidation or both.

Green tea polyphenols have demonstrated significant antioxidant, anticarcinogenic, anti-inflammatory, thermogenic, probiotic, and antimicrobial properties in numerous human, animal, and in vitro studies. [14]

Glucosamine, in the form of glucosamine sulfate, another ingredient of this compound, also contributes to weight loss. When food intake by the body occurs at a faster rate than energy consumption, the cellular concentration of adenosine triphosphate rises. Cells, however, do not store extra energy in the form of extra adenosine triphosphate. When cellular adenosine triphosphate concentrations rise because more energy (from food) is available than can be immediately used, high adenosine triphosphate concentrations inhibit glycolysis. Under conditions of high cellular adenosine triphosphate concentrations, when glycolysis is inhibited, glucose is instead converted into glycogen and fat.

When fat stored in adipose tissue is going to be used as an energy source, lipase enzymes hydrolyze triglycerides into glycerol and free fatty acids in a process called lipolysis (the breakdown of fat). These molecules (primarily the free fatty acids) serve as blood-borne energy carriers that can be used by the liver, skeletal muscles, and other organs for aerobic respiration.[15]

The effect of insulin on lipogenesis, the formation of fatty acids in the body, is blocked by glucosamine, indicating that glucosamine plays a role as a messenger for this insulin effect. [16] Insulin is secreted when there is high sugar content; insulin secretion allows for fat storage. High insulin levels trigger the hypothalamus to send hunger signals, which sets off a craving for carbohydrates; this leads one to eat more, which leads to more insulin. Excess carbohydrates are converted into glucose, and then stored as fat.

Glucose triggers a rise in insulin. Insulin acts to lower blood glucose levels, regulating those levels through several actions, including lipogenesis (conversion of carbohydrate and protein into fat). Fat cells can't be metabolized when insulin levels are normal. When you have high insulin levels, you block lipolysis and store fat. The body must initiate lipolysis to supply the cellular energy source ATP, which is necessary for muscle contraction (energy). When you reduce the level of insulin, you burn fat to provide energy. Glucosamine blocks the effect of insulin, burning up stored fat and resulting in weight loss.[17]

Scientists have yet to determine at what point in the metabolic pathway glucosamine acts to block insulin, but several studies have demonstrated this fact. A study at the Washington University School of Medicine concluded that direct administration of glucosamine can rapidly lower cellular ATP levels and affect insulin action in fat cells by independent mechanisms. [18] A University of Southern California study further explains that glucosamine induced complete and reversible insulin resistances[19]. A third study at the Albert Einstein College of Medicine adds that the etiology of peripheral insulin resistance may be distinct from the rapid and marked impairment in insulin signaling and that glucosamine on insulin-stimulated glucose metabolism is a different mechanism.[20] Essentially, the glucosamine keeps the glucose from being stored as fat, providing a temporary and reversible hyperglycemic effect that allows the glucose to be used as energy instead by blunting the insulin-induced increase in muscle glycogen content.[21] In addition to the hyperglycemic effect of glucosamine, Japanese studies on dogs and ducks demonstrate that glucosamine causes glucagon release in addition to its effect to suppress insulin release as well as its direct inhibitory effect on glucose utilization in tissues.[22]

By increasing the metabolic rate and calorie expenditure with ma huang and caffeine while simultaneously encouraging the body to use stored fat for energy, in conjunction with the carefully blended composition of other ingredients, this new product provides a unique and successful method for losing weight and increasing energy.

Curriculum Vitae

Albert M. Fleischner, Ph.D., has a doctorate in Pharmaceutical Chemistry from Rutgers University and has had over thirty years experience in the pharmaceutical industry with firms such as Schering Corporation, Lehn & Fink Division of Sterling Drugs, Bradley Pharmaceutical Corporation, Amerchol Division of CPC and the Goen Group companies. He has a number of published papers and two previously granted patents and has several patents pending.

SUMMARY

The invention discloses the formula sets that embody the invention of the supplement composition for increasing weight loss and energy levels. The combination of ephedrine and caffeine increases fat loss, maintains muscle mass, prevents the fall of HDL cholesterol during weight loss, increases insulin sensitivity, reduces lipogenesis and is safe. With the addition of glucosamine sulfate, the new and useful formula is further enhanced.

We now discuss in detail the most preferred version, variants or embodiments of the invention. First, a few words on terminology. The claim term "a" includes one and more than one. The claim term "label" is used as defined in the Federal Food Drug & Cosmetic Act and the regulations promulgated thereunder. We now turn to discussing in great detail the best (or "preferred") versions (or "embodiments") of the invention.

A representative formula for Solid-Dosage Form of Weight Loss Product is as follows, one tablet contains:

| | |
|---|---|
| Vitamin $B^6$ (as pyridoxine HCI) | 10.0 mg |
| Chromium (as chromium Chelavite ™ dinocitinate glycinate) | 200.0 mcg |
| Vanadium (as amino acid chelate) | 200.0 mcg |
| Glucosamine sulfate | 100.0 mg |
| Guarana seed and green tea leaf extracts | 910.0 (200 mg caffeine) |
| Ma huang extract | 312.5 mg (25 mg ephedrine alkaloids (aerial parts) |
| Excipients: | |
| Dicalcium Phosphate, Microcrystalline Cellulose, Croscarmellose Sodium, Stearic Acid, Magnesium Stearate, Silica, | a sufficient quantity of each to make a suitable tablet |

The scientific rationale for the formulation is as follows:

Vitamin B6 (pyridoxine) helps the body process the protein, fat and carbohydrates in our diet. It is required in the metabolization of carbohydrate, fats and proteins and has a primary role in the utilization of proteins and amino acids, converting them to carbohydrates or fats for storage or energy. Vitamin $B_6$ also helps the body resist stress. Vitamin $B_6$ activates the release of glucogen from the muscles and liver and is thus responsible for the production of biological energy. It works with other vitamins and minerals to supply the energy used in our muscles, and plays a role in cell growth.[23]

A deficiency in chromium results in glucose intolerance. Chromium contributes to the prevention of adult-onset diabetes. It has been shown to decrease sugar cravings and is considered an effective treatment against both hypoglycemia and diabetes by improving glucose tolerance, increasing cell sensitivity to insulin, and reducing circulating insulin levels.[24]

Research also indicates chromium's role in lowering total cholesterol, LDL cholesterol, and serum triglyceride levels and improves the LDL-to-HDL cholesterol ratio, according to Dr. Jeoffry Gordon in San Diego, Calif. Subsequent research supports this and suggests a greater role for chromium in the treatment and prevention of high cholesterol and cardiovascular disease. There is speculation chromium positively affects lipid profiles by its ability to increase insulin efficiency, thereby reducing elevated lipid levels.[25]

Chromium polynicotinate has been shown to possess greater biological activity and is safer than other chromium supplements. It potentiates the effects of insulin and helps overcome insulin resistance in overweight people. Chromium also seems to stimulate thermogenesis, the burning of fat, without any physical exertion.[26]

Chromium picolinate was found to cause significant chromosome damage at a non-toxic dose. In contrast, chromium polynicotinate did not cause chromosome damage at equivalent doses. Consumers are urged to switch to a nontoxic form of chromium, such as niacin-bound chromium, also known as chromium polynicotinate.[27] A 1998 study demonstrated that 9 out of 10 American diets fall short in chromium. The chromium levels of more than 40,000 men and women were measured in this study. After comparing various age groups, the study found that chromium levels plummet with the passage of time.[28] According to Dr. Michelle Rubin from the University of Maryland, in addition to increasing as we age, chromium needs rise dramatically during exercise.[29]

Vanadium is needed for cellular metabolism and for thyroid function. Research at the Grand Forks Human Nutrition Research Center suggests that vanadium is an essential nutrient beneficial for thyroid hormone metabolism.[30] A study at the University of British Columbia found that vanadium compounds could correct defective signaling pathways and increase the cells' response to insulin, which would aid normal processing of sugar in patients with diabetes.[31] Vanadium can mimic insulin. In other words, in research done with cells, it has been able to replace insulin.[32] Vanadium has recently been observed to have several physiological insulin-like effects by a post-insulin receptor kinase mechanism, making it very likely to have a favorable effect on carbohydrate metabolism.[33]

The benefits of glucosamine have already been discussed in detail, above.

Guarana and green tea seed extract (providing 200 mg of caffeine) is the first of the ingredients in the Thermogenic Herbal Concentrates group. Caffeine and the closely related alkaloids theobromine and theophylline make up the primary active agents in guarana. Caffeine's effects are well known and include stimulating the central nervous system, increasing metabolic rate and having a mild diuretic effect.[34] The tannic acid in guarana is astringent and probably accounts for its use as a digestive tonic. It is also a stimulant.[35]

The benefits of ma huang extract and its ephedrine alkaloids have been discussed above.

Without further elaboration, it is believed that one skilled in the art can, using the preceding description, utilize the present invention to its fullest extent. The specific formulas are included as a preferred embodiment of the composition formula ranges, and not to further qualify the description. Claim references to specific components include the component itself, as well as concentrates, metabolites, constituents, extracts or combinations of said ingredients.

I claim:

1. A composition of matter comprising,
   (a) glucosamine and a second component selected from the group consisting of caffeine and ephedrine;
   (b) said glucosamine and said second component present in an amount effective to aid in weight loss.

2. The composition of matter of claim 1, wherein said second component comprises both caffeine and ephedrine.

3. The composition of matter of claim 2, wherein said ingredients are present the following approximate amounts:

| | |
|---|---|
| Glucosamine | 50.0–500.0 mg |
| Caffeine | 100.0–250.0 mg |
| Ephedrine | 5.0–28.0 mg |

4. A weight loss method comprising administering a stimulant in an amount effective to increase the metabolic rate, and glucoseamine.

5. A weight loss method comprising administering glucosamine in an amount effective to promote weight loss, the dietary fiber accompanying said glucosamine, if any, being less than the amount of dietary fiber required to prevent the absorption of undigested dietary fat in the intestine.

6. The method of claim 5, said glucosamine being substantially free of dietary fiber.

7. The method of claim 5, further comprising administering a stimulant in an amount effective to promote weight loss.

* * * * *